United States Patent
Alabdullatif et al.

(10) Patent No.: US 12,175,380 B2
(45) Date of Patent: Dec. 24, 2024

(54) GAS-OIL SEPARATION PLANT VIRTUAL WATER CUT PREDICTOR BASED ON SUPERVISED LEARNING FRAMEWORK ON TIME SERIES DATA

(71) Applicant: Saudi Arabian Oil Company, Dhahran (SA)

(72) Inventors: Abdullah Mohammed Alabdullatif, Dhahran (SA); Muhammad Azmi Idris, Dhahran (SA); Mishaal Awwadh Alhetairshi, Dhahran (SA); George Andrew Wattley, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 1044 days.

(21) Appl. No.: 17/122,736

(22) Filed: Dec. 15, 2020

(65) Prior Publication Data

US 2022/0188665 A1 Jun. 16, 2022

(51) Int. Cl.
*G06N 5/04* (2023.01)
*C10G 33/08* (2006.01)
(Continued)

(52) U.S. Cl.
CPC .............. *G06N 5/04* (2013.01); *C10G 33/08* (2013.01); *G06N 20/00* (2019.01); *G16C 20/70* (2019.02); *C10G 2300/208* (2013.01)

(58) Field of Classification Search
None
See application file for complete search history.

(56) References Cited

U.S. PATENT DOCUMENTS

| 4,358,822 A | 11/1982 | Sanchez |
| 5,841,652 A | 11/1998 | Sanchez |

(Continued)

FOREIGN PATENT DOCUMENTS

WO WO 2008002345 1/2008

OTHER PUBLICATIONS

Enikeev et al., Forecast of water-cut at wells under design by machine learning methods, V International Conference on "Information Technology and Nanotechnology" (ITNT-2019), pp. 510-520 (Year: 2019).*

(Continued)

*Primary Examiner* — Alan Chen
(74) *Attorney, Agent, or Firm* — Fish & Richardson P.C.

(57) ABSTRACT

The present disclosure describes system and methods for accessing data from a gas oil separation plant (GOSP) facility, wherein the data includes measurements at various locations inside the GOSP facility and measurements of water cut of the GOSP facility; selecting, based on feature engineering, a subset of features corresponding to the measurements at various locations inside the GOSP facility, wherein the subset of features are more likely to impact the water cut of the GOSP facility than unselected features; and based on the subset of features, training a predictive model capable of predicting the water cut of the GOSP facility based on the measurements of water cut of the GOSP facility, wherein the training is based on, at least in part, (i) a subset of the measurements at various locations inside the GOSP facility and (ii) a subset of the measurements of water cut of the GOSP facility.

14 Claims, 7 Drawing Sheets

(51) Int. Cl.
*G06N 20/00* (2019.01)
*G16C 20/70* (2019.01)

(56) References Cited

U.S. PATENT DOCUMENTS

| | | | |
|---|---|---|---|
| 6,056,781 | A | 5/2000 | Wassick et al. |
| 6,185,470 | B1 | 2/2001 | Pado et al. |
| 6,611,735 | B1 | 8/2003 | Henly et al. |
| 7,072,797 | B2 | 7/2006 | Gorinevsky |
| 7,437,323 | B1 | 10/2008 | Valkov et al. |
| 7,752,023 | B2 | 7/2010 | Middya |
| 8,473,268 | B2 | 6/2013 | Benish et al. |
| 8,641,813 | B2 | 2/2014 | Gysling |
| 9,074,465 | B2 | 7/2015 | Abivin et al. |
| 9,092,124 | B2 | 7/2015 | Amminudin et al. |
| 9,778,091 | B2 | 10/2017 | Fraser et al. |
| 9,784,198 | B2 | 10/2017 | Long et al. |
| 10,416,015 | B2 | 9/2019 | Xie et al. |
| 10,670,575 | B2 | 6/2020 | Hollaender et al. |
| 2004/0181498 | A1 | 9/2004 | Kothare et al. |
| 2006/0247900 | A1 | 11/2006 | Brocklebank |
| 2009/0204237 | A1 | 8/2009 | Sustaeta et al. |
| 2012/0290104 | A1 | 11/2012 | Holt et al. |
| 2015/0324329 | A1 | 11/2015 | Blevins et al. |
| 2016/0333686 | A1 | 11/2016 | Scott |

OTHER PUBLICATIONS

Mahmoud et al., Intelligent prediction of optimum separation parameters in the multistage crude oil production facilities; Journal of Petroleum Exploration and Production Technology (2019) 9:2979-2995 (Year: 2019).*

Liu et al., Predictive model for water absorption in sublayers using a machine learning method, Journal of Petroleum Science and Engineering 182 (2019), pp. 1-11 (Year: 2019).*

Beggs, "Gas Production Operations, section Piping System performance: Flow in Pipelines," Oil and Gas Consultants International Inc., OGCI Publications, Jul. 1984, 333 pages.

Bokhamseen et al., "Utilization of numerical optimization to model gas condensate flow through chokes in a rich gas condensate reservoir in Saudi Arabia," SPE 177694-MS, Society of Petroleum Engineers (SPE), presented at the Abu Dhabi International Petroleum Exhibition and Conference, Nov. 9-12, 2015, 13 pages.

Gilbert, "Flowing and Gas-Lift Well Performance," presented at the spring meeting of the Pacific Coast Distric, Division of Production, May 1954, Drilling and Production Prac., 1954, 32 pages.

Shalev-Shwartz and Shai, "Understanding Machine Learning: from Theory to Algorithms," Cambridge University Press, 2014, 449 pages.

Taiyr et al., "Developing the effective production allocation workflow using different approaches for gas condensate reservoir," SPE 140016, Society of Petroleum Engineers (SPE), presented at the SPE Caspian Carbonates Technology Conference, Atyrau, Kazakhstan, Nov. 8-10, 2010, 16 pages.

Xia et al., "A Soft Sensor for Water-Content-in-Oil Based on GA-RBF Neural Network," Measurement and Control, Jul. 2010, 43:6 (179-182), 4 pages.

* cited by examiner

GAS-OIL SEPARATION PLANT VIRTUAL WATER CUT PREDICTOR BASED ON SUPERVISED LEARNING FRAMEWORK ON TIME SERIES DATA

TECHNICAL FIELD

This disclosure generally relates to water cut prediction of a gas-oil separation plant (GOSP).

BACKGROUND

A gas-oil separation plant (GOSP) is a separation facility designed to separate the water and gas from crude oil.

SUMMARY

In one aspect, some implementations provide a computer-implemented method that includes: accessing data from a gas oil separation plant (GOSP) facility, wherein the data includes measurements at various locations inside the GOSP facility and measurements of water cut of the GOSP facility; selecting, based on feature engineering, a subset of features corresponding to the measurements at various locations inside the GOSP facility, wherein the subset of features are more likely to impact the water cut of the GOSP facility than unselected features; and based on the subset of features, training a predictive model capable of predicting the water cut of the GOSP facility based on the measurements of water cut of the GOSP facility, wherein the training is based on, at least in part, (i) a subset of the measurements at various locations inside the GOSP facility and (ii) a subset of the measurements of water cut of the GOSP facility.

Implementations may include one or more of the following features.

The computer-implemented method may further include: allocating the predictive model to predict at least one water cut of the GOSP facility based on at least one measurement taken from inside the GOSP facility. The at least one measurement taken from inside the GOSP facility may not be included the subset of the measurements at various locations inside the GOSP facility, and wherein the at least one water cut of the GOSP facility is not included in the subset of the measurements of water cut of the GOSP facility. The at least one measurement taken from inside the GOSP facility may be obtained after the predictive model has been trained. The method may further include: dynamically presenting the at least one water cut of the GOSP facility on a dashboard, wherein the dashboard plots the at least one water cut of the GOSP facility as the at least one measurement taken from inside the GOSP facility becomes available.

The features may be selected based on at least one decision tree algorithm that utilizes a Gini importance metric or a mean decrease impurity (MDI) metric. The decision tree algorithm may assign a score to each of the features based on how useful each feature is at predicting the water cut of the GOSP facility. The decision tree algorithm may utilize at least one permutation of importance against the predictive model being trained. The at least one permutation of importance may perform shuffling of the features according to respective scores of the features. The method may further comprise: evaluating an importance of each feature; and ranking the features based on the evaluated importance. The method may further include: identifying features that are strongly correlated such that duplicate features can be trimmed, wherein the features are strongly correlated when a correlation of the features exceed a threshold.

In another aspect, some implementations provide a computer system comprising one or more processors, wherein the one or more processors are configured to perform operations of: accessing data from a gas oil separation plant (GOSP) facility, wherein the data includes measurements at various locations inside the GOSP facility and measurements of water cut of the GOSP facility; selecting, based on feature engineering, a subset of features corresponding to the measurements at various locations inside the GOSP facility, wherein the subset of features are more likely to impact the water cut of the GOSP facility than unselected features; and based on the subset of features, training a predictive model capable of predicting the water cut of the GOSP facility based on the measurements of water cut of the GOSP facility, wherein the training is based on, at least in part, (i) a subset of the measurements at various locations inside the GOSP facility and (ii) a subset of the measurements of water cut of the GOSP facility.

Implementations may include one or more of the following features.

The operations may further include: allocating the predictive model to predict at least one water cut of the GOSP facility based on at least one measurement taken from inside the GOSP facility. The at least one measurement taken from inside the GOSP facility may not be included the subset of the measurements at various locations inside the GOSP facility, and wherein the at least one water cut of the GOSP facility is not included in the subset of the measurements of water cut of the GOSP facility. The at least one measurement taken from inside the GOSP facility may be obtained after the predictive model has been trained. The operations may further include: dynamically presenting the at least one water cut of the GOSP facility on a dashboard, wherein the dashboard plots the at least one water cut of the GOSP facility as the at least one measurement taken from inside the GOSP facility becomes available.

The features may be selected based on at least one decision tree algorithm that utilizes a Gini importance metric or a mean decrease impurity (MDI) metric. The decision tree algorithm may assign a score to each of the features based on how useful each feature is at predicting the water cut of the GOSP facility. The decision tree algorithm may utilize at least one permutation of importance against the predictive model being trained. The at least one permutation of importance may perform shuffling of the features according to respective scores of the features. The operations may further include: evaluating an importance of each feature; and ranking the features based on the evaluated importance. The operations may further include: identifying features that are strongly correlated such that duplicate features can be trimmed, wherein the features are strongly correlated when a correlation of the features exceed a threshold.

Implementations according to the present disclosure may be realized in computer implemented methods, hardware computing systems, and tangible computer readable media. For example, a system of one or more computers can be configured to perform particular actions by virtue of having software, firmware, hardware, or a combination of them installed on the system that in operation causes or cause the system to perform the actions. One or more computer programs can be configured to perform particular actions by virtue of including instructions that, when executed by data processing apparatus, cause the apparatus to perform the actions.

The details of one or more implementations of the subject matter of this specification are set forth in the description, the claims, and the accompanying drawings. Other features, aspects, and advantages of the subject matter will become apparent from the description, the claims, and the accompanying drawings.

DESCRIPTION OF DRAWINGS

Like reference numbers and designations in the various drawings indicate like elements.

DETAILED DESCRIPTION

The disclosed technology is directed to computerized method of predicting water cut from a gas-oil separation plant (GOSP). A GOSP is a separation facility designed to separate the water and gas from crude oil. In some cases, the GOSP is designed with an objective to produce crude oil meeting corporate specification value of, for example, 0.2% basic sediment and water (BS&W) in the oil outlet. To achieve such the oil specification, a physical analyzer is used to provide real time values of the BS&W. Such real time values of the BS&W are often referred to as water cut, which is a crude quality measurement of great significance.

The implementations generally employ advanced analytics and, specifically, predictive analytics. In particular, these implementations include a system or method for predicting current as well as future readings of the water cut in crude oil. Some implementations include the method of developing virtual water cut analyzer by utilizing machine learning techniques and algorithm to predict and forecast water-cut reading. Some implementations include a system that is data-driven, the performance of which can be improved with time by incorporating new data points.

Some implementations includes retrieving time series data from the GOSP process and utilizing supervised machine learning that includes, for example, data engineering techniques and regression and classification algorithms. These implementations can further generate synthetic features by utilizing statistics within specific time windows of the time series process variable data. In some cases, these implementations can generate prediction results using regression and classification algorithms including forecast of water cut for the upcoming 15 to 30 minutes and a list of influential features that are significant to the prediction. In these cases, the prediction and forecast of the water cut are generated through alert and visualization.

In more detail, the implementations generate synthetic features from process variables in the time series format. The synthetic features, as used in the present disclosure, can refer to input variables generated by calculating statistics on the observed process variables. Such synthetic features can allow rich statistical features to be generated based on specific time windows for individual process variables. The new generated structure is then used in ensemble-decision-tree based algorithms to predict numerical values of water cut using regression. In addition, the new generated features can be used in a classification machine learning approach to forecast categorical values that represent predefined water cut ranges. In one example, the system receives data encoding process variables, generates the synthetic features as part of a feature engineering process where more features can be extracted from the existing data, and then predicts the water-cut and forecast the reading ranges for the next 15 to 30 minutes. In addition, the system generates list of most influential features.

The terminology used in the present disclosure includes the following terms.

The term "water cut" refers to the measurement of water content in liquid hydrocarbons as percentage of the volume.

The term "process variables" refers to measurements of hydrocarbons process stages or sensor readings throughout the hydrocarbons separation process, all related to the water cut values.

The term "predictive analytics" refers to the use of machine learning and applied statistics to predict unknown conditions based on the available data. Two general areas that fall under predictive analytics are classification and regression. While classification refers to the prediction of categorical values, regression connotes the prediction of continuous numerical values.

One machine learning implementation is also known as "supervised learning" where the "correct" target or y values are available. For illustration, the goal of some implementations is to learn from the available data to predict the unknown values with some defined error metrics. In supervised learning, for example, there are a set of known predictors (features) $x_1, x_2, \ldots, x_m$ which are known to the system as well as the target values $y_1, y_2, \ldots, y_n$, which are to be inferred. The system's objective is to train a machine learning model to predict new target values $y_1, y_2, \ldots, y_n$ by observing new features.

The implementations can employ a variety of supervised learning algorithms. For classification, examples of prediction algorithms can include, logistic regression, decision trees, nearest neighbor, support vector machines, and neural networks. For regression, examples of predication algorithms can include least squares regression, Lasso, and others. The performance of an algorithm can depend on a number factors, such as the selected set of features, training/validation method and hyper-parameters tuning. As such, predictive analytics can manifest as an iterative approach of knowledge finding and includes trial and error. An iterative approach can iteratively modify data preprocessing and model parameters until the result achieves the desired properties.

The term "feature engineering" refers to the process of manipulating input features before using them in machine learning development.

Figure 1:
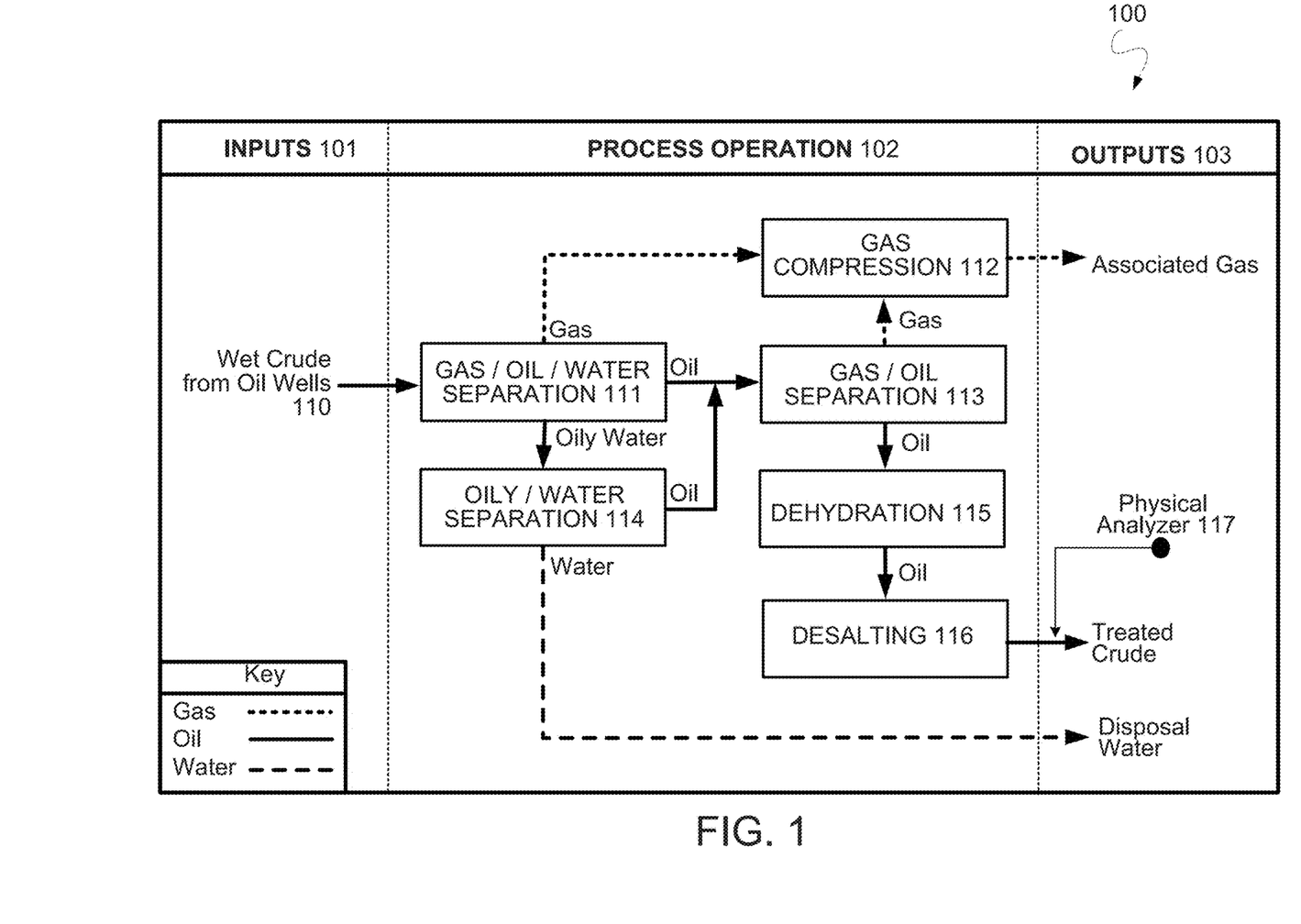
FIG. 1 shows an example of a GOSP facility according to an implementation of the present disclosure.

Referring to FIG. 1, an example of a feature generation diagram 100 shows inputs 101, process operation 102 that operates on inputs 101, and outputs 103 from process operation 102. Input 101 includes wet crude from oil wells 110, which feeds into gas/oil/water separation module 111 to provide gas, oil, and oily water. As a result of processing performed by separation module 111, gas is channeled to gas compression module 112, oil is channeled to gas/oil separation module 113, and oily water is channeled to oil/water separation module 114. Here, gas/oil separation module 113 further provides separated gas to gas compression module 112, and oil to dehydration module 115. Gas compression module 112 provides associated gas as an output. Dehydration module 115 provides oil to desalting module 116, which provides treated crude as an output. Oil/water separation module 114 processes the oily water to provide oil to gas/oil separation module 113 and water as disposal water as an output. As illustrated, a physical analyzer 117 is installed to inspect the treated crude.

Various implementations can utilize predictive modeling. In particular, the implementations operate on a set of known process variables $X_1, X_2, \ldots, X_m$ and a known water cut target variable y, train machine learning models based on programming, and predict new water cut values. Specifically, implementations may incorporate feature engineering for supervised machine learning models to predict water cut by calculating statistics of the time series data for process variables for a specific time period, and using the statistics as inputs to train machine learning models and predict new water cut values.

Figure 2:
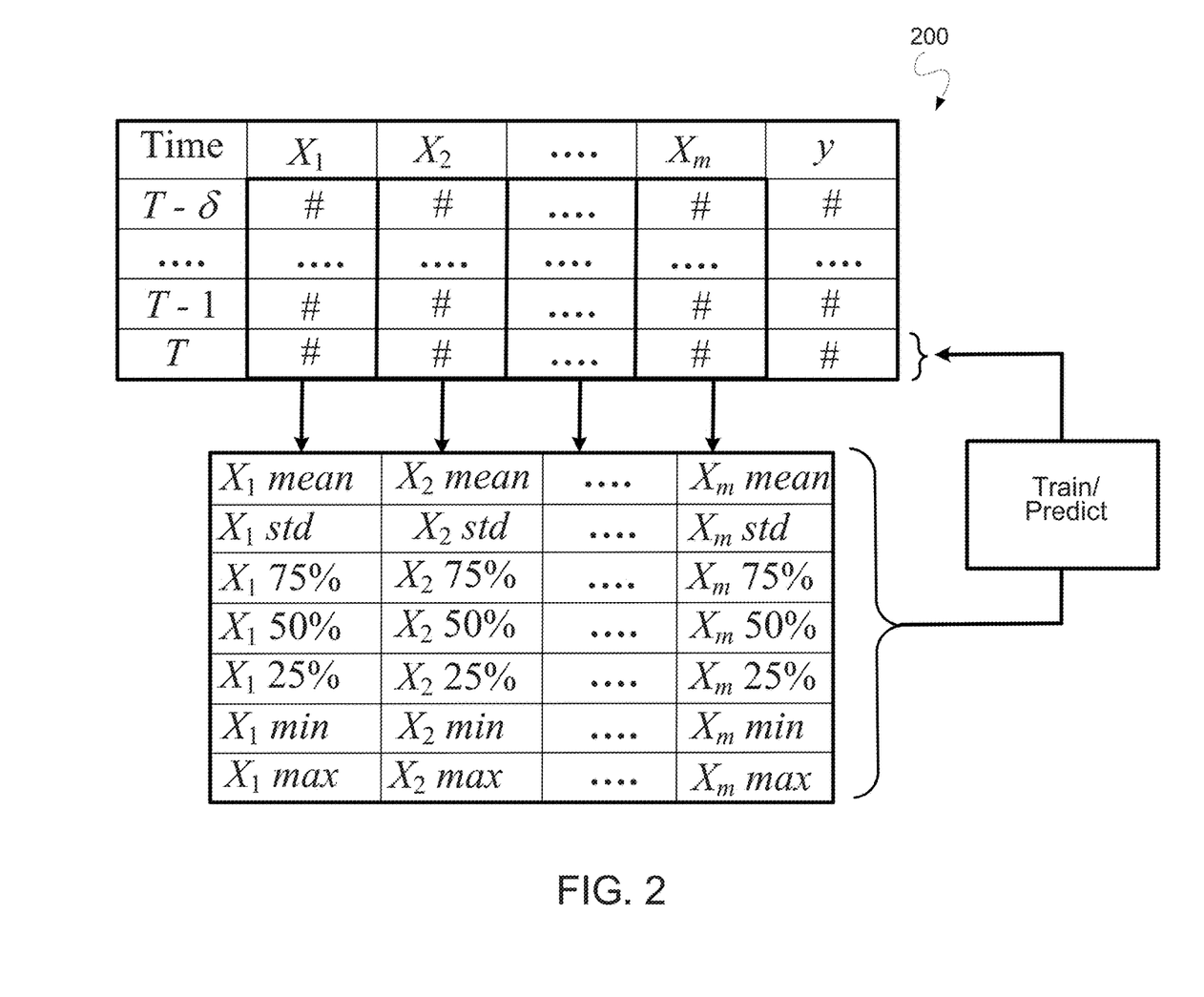
FIG. 2 illustrates an example of a feature diagram according to an implementation of the present disclosure.

FIG. 2 illustrates an example of a feature diagram 200 according to some implementations of the present disclosure. The first column shows a time series from T−δ, to T. Here, δ is the lead time, which can be selected empirically based on the plant setup and process engineering knowledge. In some cases, the lead time can be the time that it would take the process fluid to travel from the point of measurement to the physical analyzer installed in the treated crude stream, an example of which is shown in FIG. 1. The next m columns show process variables $X_1, X_2, \ldots, X_m$. In some cases, these process variables may represent actual measurements taken from the crude treatment stream, as illustrated in FIG. 1. The last column represents output y, which can represent actual measurement of the water cut ratio. Here, the process variables can be selected based on subject matter expertise and a combination of feature engineering techniques such as ensemble learning feature importance and permutation. Some implementations calculate statistics for each process variable X to predict y at time T. Example of the statistics includes but not limited to mean, median, standard deviation, min and max. Output value y can include, for example, measurements taken at the physical analyzer 117. In some cases, y can be a vector.

In more detail, the second row represents the time instant at T−δ, the values of process variables $X_1, X_2, \ldots, X_m$, and the value of output y at this time instant. The remaining rows likewise show a subsequent time instant as well as the process variables and the output at such time instant. In some implementations, the statistic characteristics of these process variables $X_1, X_2, \ldots, X_m$ can include mean, standard deviation, 75% percentile, 50% percentile, and 25% percentile, minimum, and maximum. These implementations may incorporate decision tree based algorithms that utilize Gini importance or mean decrease impurity (MDI) for feature selection. Feature importance refers to techniques that assign a score to input features based on how useful they are at predicting a target variable. Feature importance scores can provide insight into the data, insight into the model, and the basis for dimensionality reduction and feature selection that can improve the efficiency and effectiveness of a predictive model on the problem. Implementations can also use permutation importance against the same model by shuffling the value of each feature and evaluating the performance of the model. By doing permutation importance, the importance of each feature can be evaluated and ranked. In some implementations, features that have been identified as strongly correlated can be removed. The removal can facilitate not only identifying the influential features (process variables), but also enabling the ranking accordingly. Implementations may incorporate the aforementioned techniques in the feature selection process.

Figure 3:
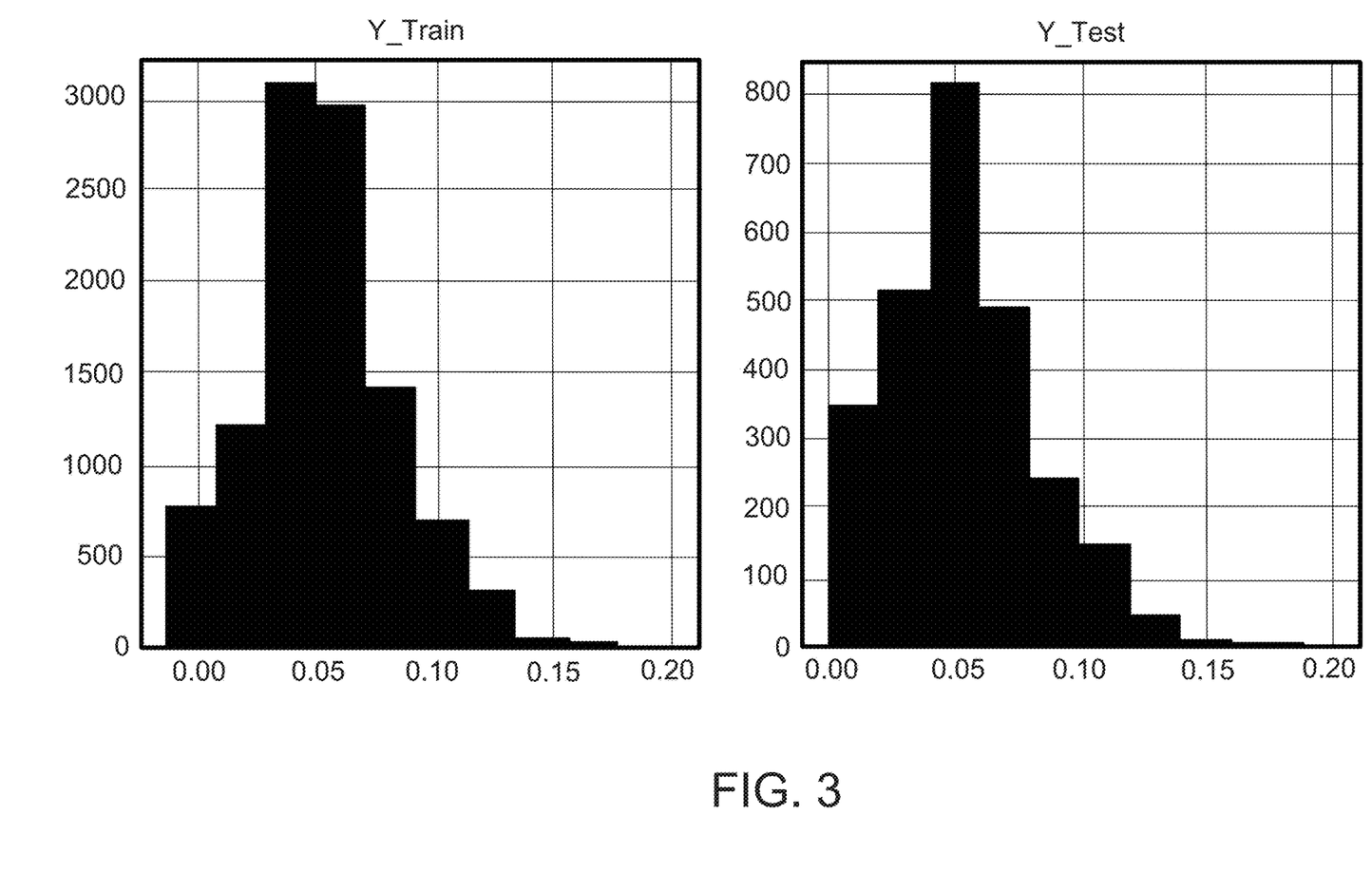
FIG. 3 is an example of showing training and testing according to an implementation of the present disclosure.

Using the generated features, some implementations may train supervised learning models, based on which to predict water cut values for new data points. Referring to FIG. 3, some implementations may split the available data into a training subset (left panel) and test subset (right panel). For example, 80% of the available historical data can be allocated to the training subset to train a predictive model while the 20% of the available historical data can be used to evaluate the accuracy of the predictive model. In this example, the target range can be limited to a range of, for example, 0.0 to 0.2 such that values outside this range are considered outliers with insufficient records for model building. In some cases, the target is shifted in time to accommodate process delay, i.e., the lead time that the system takes to take effect.

Figure 4A:
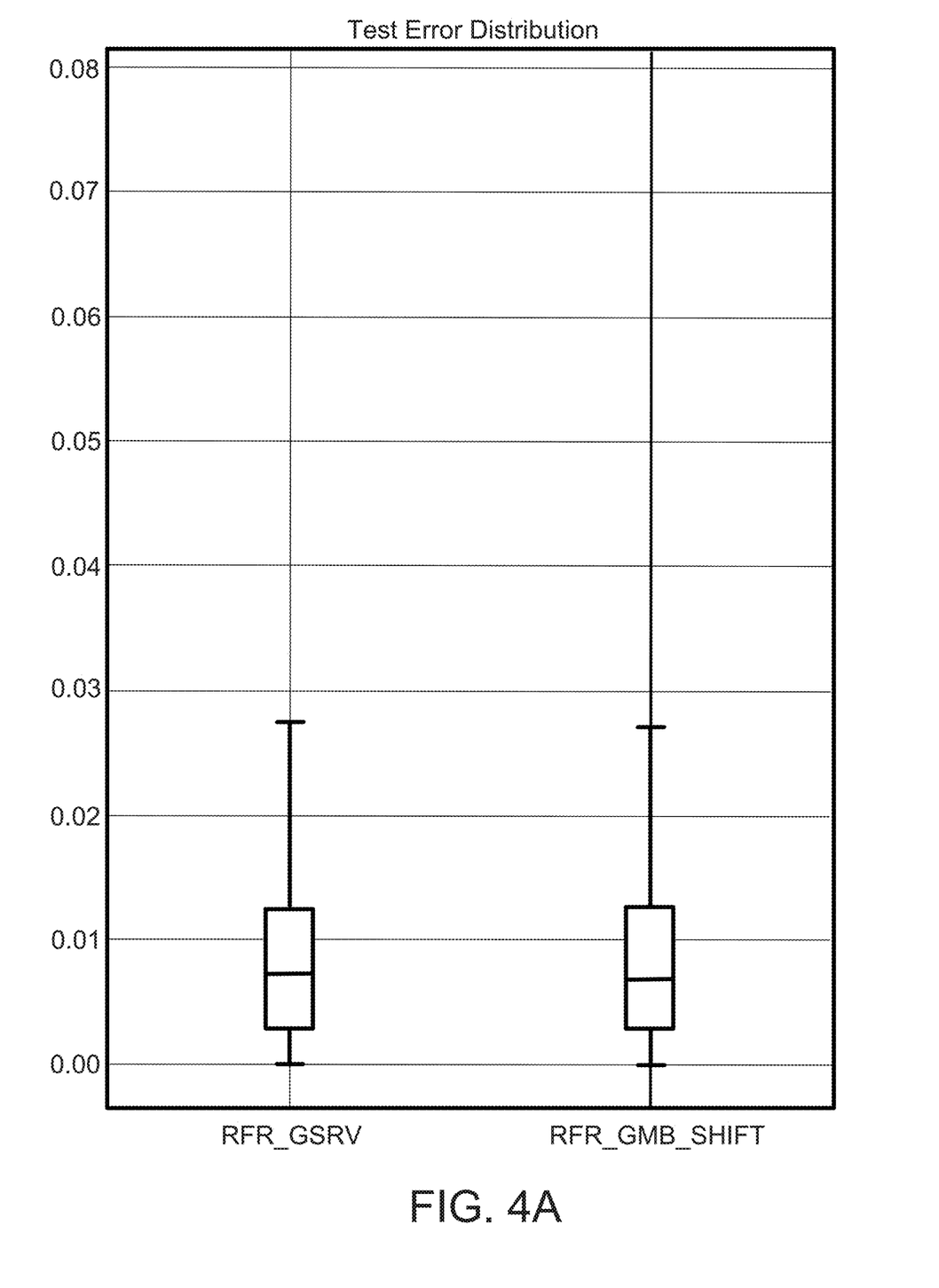
FIGS. 4A-4B illustrate examples of model evaluation for feature generation according to an implementation of the present disclosure.
Figure 4B:
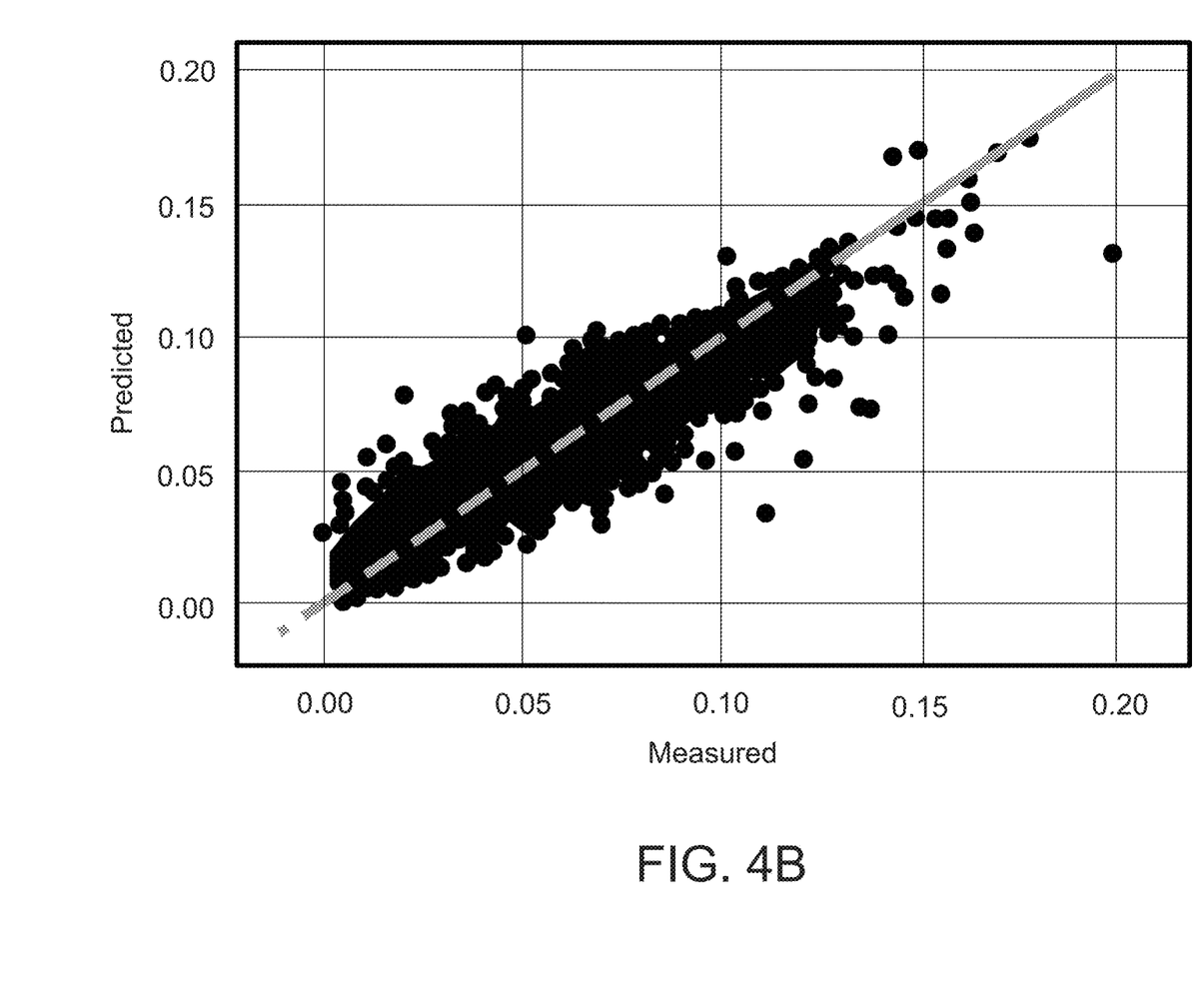

Referring to FIGS. 4A and 4B, examples of results for evaluating predictive models using test data are demonstrated. FIG. 4A particularly shows test error distribution for two predictive models constructed. FIG. 4B, on the other hand, shows the distribution of measured data and predicted data across a line of identity. In one implementation, the output generated by the system is presented to the user in the form of a report or a dashboard. The dashboard plots the predicted target y. The output may also highlight the most influential environment conditions by absolute value.

Some implementations can incorporate decision tree based algorithms which utilize a Gini importance metric or a mean decrease impurity (MDI) metric for feature selection. For example, a random forest representation can characterize the feature space as a tree of nodes, each node corresponding to a candidate process variable from FIG. 2. Gini Importance or Mean Decrease in Impurity (MDI) may generally calculate each feature importance as the sum over the number of splits (across all tress) that include the feature, proportionally to the number of samples it splits. In some implementations, the Gini importance or the MDI can be calculated as the total decrease in node impurity (weighted by the probability of reaching that node (which is approximated by the proportion of samples reaching that node)) averaged over all trees of the ensemble. Implementations may additionally utilize permutation importance against the same model by shuffling the value of each feature and evaluating the performance of the model. By doing permutation importance, the importance of each feature can be estimated and ranked.

Some implementations can include a system with multiple modular components, such as a data collection module, data pre-processing module and statistical modeling module. The system can implement a flow chart 500 illustrated in FIG. 5. The flow chart may start by compiling the list of process variables involved in oil-gas separation process (501). For example, historical data collected in the form ($y_t$, $X_t$) can be gathered, where $y_t$ is the target, $X_t$ is the input parameter, and t is the time instant.

Figure 5:
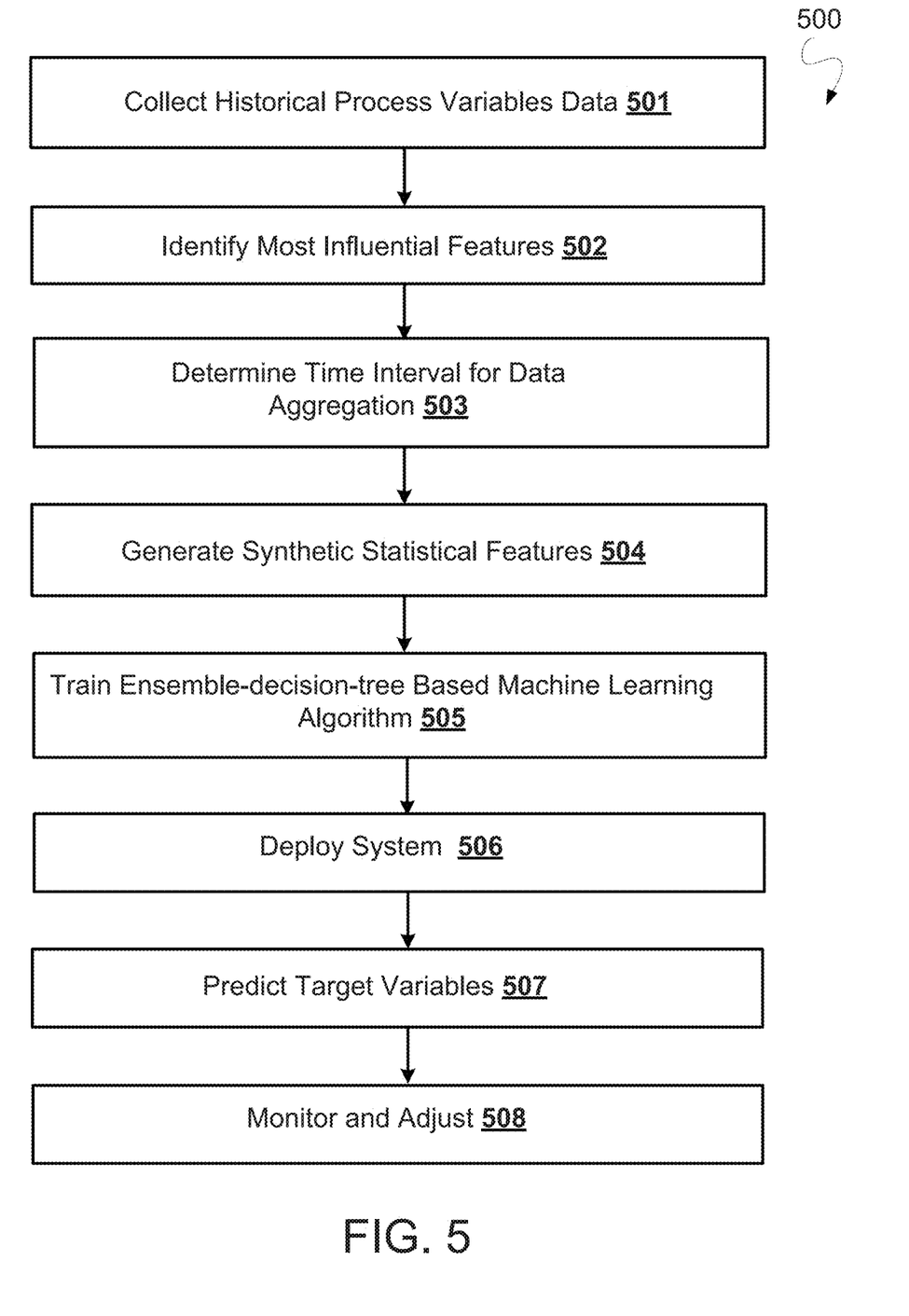
FIG. 5 illustrates an example of a flow chart according to an implementation of the present disclosure.

Thereafter, the most influential process variables are identified (502). In some cases, the identification is based on correlation analysis, feature importance, and permutation techniques from ensemble-decision-tree based algorithm. Specifically, implementations can incorporate decision tree based algorithms which use Gini importance or mean decrease impurity (MDI) for feature selection. Additionally, the decision tree based algorithms can incorporate permutation importance against the same model by shuffling the value of each feature and evaluate the performance of the model. The permutation importance evaluation can estimate the importance of each feature and rank the features accordingly. Moreover, features that are strongly correlated can be removed to streamline not only the process to identify the influential features (process variables), but also facilitate the subsequent ranking. In some cases, the features are strongly correlated when the correlation of the features exceed a threshold. The threshold can be pre-determined. The list of process variables is thus reduced to those that may have significant impact on the prediction y.

Next, time interval for data aggregation is determined (503). The time interval can be, for example, a time period spanning several minutes to hours. Time intervals can be selected by a user through a user interface or defined upfront for specific GOSP facilities.

Subsequently, synthetic statistical features are generated (504). The features can be generated based on the operation variables within the time frame decided from the previous steps.

Next, the data is trained on a decision-tree based algorithm and the best statistical model is selected for prediction (505). Examples of decision-tree based algorithm can include ensemble methods, bagging methods, and boosting methods. Examples of ensemble methods can combine several decision trees to produce better predictive performance than a single decision tree. Under the ensemble model, a group of weak learners can come together to form a strong learner. Examples of bagging methods can create models from subset of data (trees) and average prediction from these trees (models) which has robust result compared to single tree. For context, a random forest is an extension over a bagging method. Examples of boosting methods can create collection of predictors or learners. The learners learn sequentially with early learners fitting simple models to the data and then analyzing data for errors. Consecutive trees (models) are trained at every step where the goal is to solve net error from the prior tree. Gradient boosting is an extension over a boosting method.

When the system is trained to generate new predictions, the system can be deployed (506) in a production setting to predict target variables (507). During this deployment, the system can be monitored for its performance and the predictive model can be adjusted accordingly based on, for example, comparing the actual output with the predicted output (508).

Figure 6:
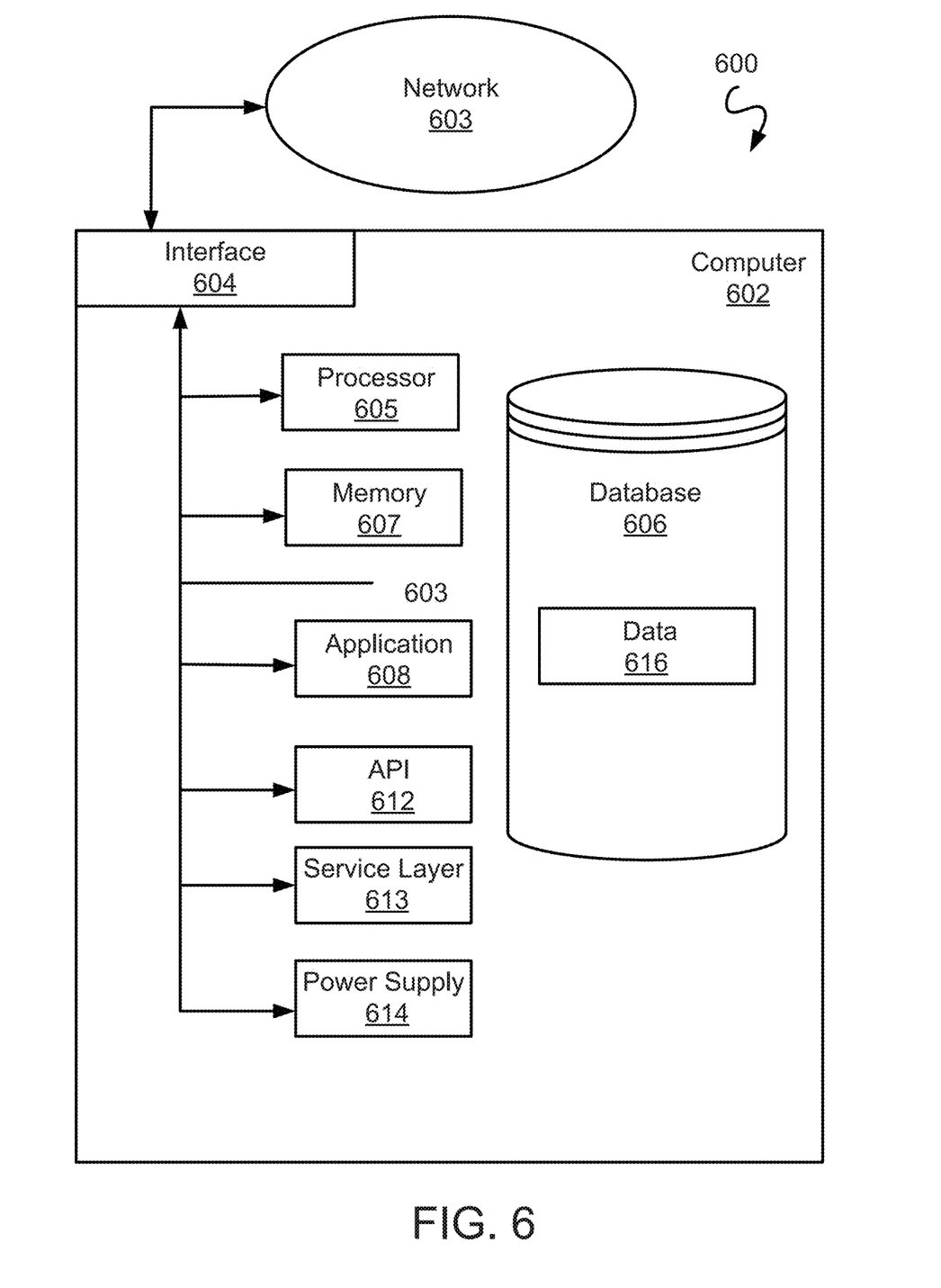
FIG. 6 is a block diagram illustrating an example of a computer system used to provide computational functionalities associated with described algorithms, methods, functions, processes, flows, and procedures, according to an implementation of the present disclosure.

FIG. 6 is a block diagram illustrating an example of a computer system 600 used to provide computational functionalities associated with described algorithms, methods, functions, processes, flows, and procedures, according to an implementation of the present disclosure. The illustrated computer 602 is intended to encompass any computing device such as a server, desktop computer, laptop/notebook computer, wireless data port, smart phone, personal data assistant (PDA), tablet computing device, one or more processors within these devices, another computing device, or a combination of computing devices, including physical or virtual instances of the computing device, or a combination of physical or virtual instances of the computing device. Additionally, the computer 602 can comprise a computer that includes an input device, such as a keypad, keyboard, touch screen, another input device, or a combination of input devices that can accept user information, and an output device that conveys information associated with the operation of the computer 602, including digital data, visual, audio, another type of information, or a combination of types of information, on a graphical-type user interface (UI) (or GUI) or other UI.

The computer 602 can serve in a role in a computer system as a client, network component, a server, a database or another persistency, another role, or a combination of roles for performing the subject matter described in the present disclosure. The illustrated computer 602 is communicably coupled with a network 603. In some implementations, one or more components of the computer 602 can be configured to operate within an environment, including cloud-computing-based, local, global, another environment, or a combination of environments.

The computer 602 is an electronic computing device operable to receive, transmit, process, store, or manage data and information associated with the described subject matter. According to some implementations, the computer 602 can also include or be communicably coupled with a server, including an application server, e-mail server, web server, caching server, streaming data server, another server, or a combination of servers.

The computer 602 can receive requests over network 603 (for example, from a client software application executing on another computer 602) and respond to the received requests by processing the received requests using a software application or a combination of software applications. In addition, requests can also be sent to the computer 602 from internal users, external or third-parties, or other entities, individuals, systems, or computers.

Each of the components of the computer 602 can communicate using a system bus 603. In some implementations, any or all of the components of the computer 602, including hardware, software, or a combination of hardware and software, can interface over the system bus 603 using an application programming interface (API) 612, a service layer 613, or a combination of the API 612 and service layer 613. The API 612 can include specifications for routines, data structures, and object classes. The API 612 can be either computer-language independent or dependent and refer to a complete interface, a single function, or even a set of APIs. The service layer 613 provides software services to the computer 602 or other components (whether illustrated or not) that are communicably coupled to the computer 602. The functionality of the computer 602 can be accessible for all service consumers using this service layer. Software services, such as those provided by the service layer 613, provide reusable, defined functionalities through a defined interface. For example, the interface can be software written in JAVA, C++, another computing language, or a combination of computing languages providing data in extensible markup language (XML) format, another format, or a combination of formats. While illustrated as an integrated component of the computer 602, alternative implementations can illustrate the API 612 or the service layer 613 as stand-alone components in relation to other components of the computer 602 or other components (whether illustrated or not) that are communicably coupled to the computer 602. Moreover, any or all parts of the API 612 or the service layer 613 can be implemented as a child or a sub-module of another software module, enterprise application, or hardware module without departing from the scope of the present disclosure.

The computer 602 includes an interface 604. Although illustrated as a single interface 604 in FIG. 6, two or more interfaces 604 can be used according to particular needs, desires, or particular implementations of the computer 602. The interface 604 is used by the computer 602 for communicating with another computing system (whether illustrated or not) that is communicatively linked to the network 603 in a distributed environment. Generally, the interface 604 is operable to communicate with the network 603 and comprises logic encoded in software, hardware, or a combination of software and hardware. More specifically, the interface 604 can comprise software supporting one or more communication protocols associated with communications such that the network 603 or interface's hardware is operable to communicate physical signals within and outside of the illustrated computer 602.

The computer 602 includes a processor 605. Although illustrated as a single processor 605 in FIG. 6, two or more processors can be used according to particular needs, desires, or particular implementations of the computer 602. Generally, the processor 605 executes instructions and manipulates data to perform the operations of the computer 602 and any algorithms, methods, functions, processes, flows, and procedures as described in the present disclosure.

The computer 602 also includes a database 606 that can hold data for the computer 602, another component communicatively linked to the network 603 (whether illustrated or not), or a combination of the computer 602 and another component. For example, database 606 can be an in-memory, conventional, or another type of database storing data consistent with the present disclosure. In some implementations, database 606 can be a combination of two or more different database types (for example, a hybrid in-memory and conventional database) according to particular needs, desires, or particular implementations of the computer 602 and the described functionality. Although illustrated as a single database 606 in FIG. 6, two or more databases of similar or differing types can be used according to particular needs, desires, or particular implementations of the computer 602 and the described functionality. While database 606 is illustrated as an integral component of the computer 602, in alternative implementations, database 606 can be external to the computer 602. As illustrated, the database 606 holds the previously described data 616 including, for example, multiple streams of data from various sources, such as the crude extraction process as outlined in FIG. 1.

The computer 602 also includes a memory 607 that can hold data for the computer 602, another component or components communicatively linked to the network 603 (whether illustrated or not), or a combination of the computer 602 and another component. Memory 607 can store any data consistent with the present disclosure. In some implementations, memory 607 can be a combination of two or more different types of memory (for example, a combination of semiconductor and magnetic storage) according to particular needs, desires, or particular implementations of the computer 602 and the described functionality. Although illustrated as a single memory 607 in FIG. 6, two or more memories 607 or similar or differing types can be used according to particular needs, desires, or particular implementations of the computer 602 and the described functionality. While memory 607 is illustrated as an integral component of the computer 602, in alternative implementations, memory 607 can be external to the computer 602.

The application 608 is an algorithmic software engine providing functionality according to particular needs, desires, or particular implementations of the computer 602, particularly with respect to functionality described in the present disclosure. For example, application 608 can serve as one or more components, modules, or applications. Further, although illustrated as a single application 608, the application 608 can be implemented as multiple applications 608 on the computer 602. In addition, although illustrated as integral to the computer 602, in alternative implementations, the application 608 can be external to the computer 602.

The computer 602 can also include a power supply 614. The power supply 614 can include a rechargeable or non-rechargeable battery that can be configured to be either user- or non-user-replaceable. In some implementations, the power supply 614 can include power-conversion or management circuits (including recharging, standby, or another power management functionality). In some implementations, the power-supply 614 can include a power plug to allow the computer 602 to be plugged into a wall socket or another power source to, for example, power the computer 602 or recharge a rechargeable battery.

There can be any number of computers 602 associated with, or external to, a computer system containing computer 602, each computer 602 communicating over network 603. Further, the term "client," "user," or other appropriate terminology can be used interchangeably, as appropriate, without departing from the scope of the present disclosure. Moreover, the present disclosure contemplates that many users can use one computer 602, or that one user can use multiple computers 602.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs, that is, one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal, for example, a machine-generated electrical, optical, or electromagnetic signal that is generated to encode information for transmission to a receiver apparatus for execution by a data processing apparatus. The computer-storage medium can be a machine-readable storage device, a machine-readable storage substrate, a random or serial access memory device, or a combination of computer-storage mediums. Configuring one or more computers means that the one or more computers have installed hardware, firmware, or software (or combinations of hardware, firmware, and software) so that when the software is executed by the one or more computers, particular computing operations are performed.

The term "real-time," "real time," "realtime," "real (fast) time (RFT)," "near(ly) real-time (NRT)," "quasi real-time," or similar terms (as understood by one of ordinary skill in the art), means that an action and a response are temporally proximate such that an individual perceives the action and the response occurring substantially simultaneously. For example, the time difference for a response to display (or for an initiation of a display) of data following the individual's action to access the data can be less than 1 millisecond (ms), less than 1 second (s), or less than 5 s. While the requested data need not be displayed (or initiated for display) instantaneously, it is displayed (or initiated for display) without any intentional delay, taking into account processing limitations of a described computing system and time required to, for example, gather, accurately measure, analyze, process, store, or transmit the data.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be, or further include special purpose logic circuitry, for example, a central processing unit (CPU), an FPGA (field programmable gate array), or an ASIC (application-specific integrated circuit). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with an operating system of some type, for example LINUX, UNIX, WINDOWS, MAC OS, ANDROID, IOS, another operating system, or a combination of operating systems.

A computer program, which can also be referred to or described as a program, software, a software application, a unit, a module, a software module, a script, code, or other component can be written in any form of programming language, including compiled or interpreted languages, or declarative or procedural languages, and it can be deployed in any form, including, for example, as a stand-alone program, module, component, or subroutine, for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network.

While portions of the programs illustrated in the various figures can be illustrated as individual components, such as units or modules, that implement described features and functionality using various objects, methods, or other processes, the programs can instead include a number of sub-units, sub-modules, third-party services, components, libraries, and other components, as appropriate. Conversely, the features and functionality of various components can be combined into single components, as appropriate. Thresholds used to make computational determinations can be statically, dynamically, or both statically and dynamically determined.

Described methods, processes, or logic flows represent one or more examples of functionality consistent with the present disclosure and are not intended to limit the disclosure to the described or illustrated implementations, but to be accorded the widest scope consistent with described principles and features. The described methods, processes, or logic flows can be performed by one or more programmable computers executing one or more computer programs to perform functions by operating on input data and generating output data. The methods, processes, or logic flows can also be performed by, and apparatus can also be implemented as, special purpose logic circuitry, for example, a CPU, an FPGA, or an ASIC.

Computers for the execution of a computer program can be based on general or special purpose microprocessors, both, or another type of CPU. Generally, a CPU will receive instructions and data from and write to a memory. The essential elements of a computer are a CPU, for performing or executing instructions, and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable memory storage device.

Non-transitory computer-readable media for storing computer program instructions and data can include all forms of media and memory devices, magnetic devices, magneto optical disks, and optical memory device. Memory devices include semiconductor memory devices, for example, random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Magnetic devices include, for example, tape, cartridges, cassettes, internal/removable disks. Optical memory devices include, for example, digital video disc (DVD), CD-ROM, DVD+/−R, DVD-RAM, DVD-ROM, HD-DVD, and BLURAY, and other optical memory technologies. The memory can store various objects or data, including caches, classes, frameworks, applications, modules, backup data, jobs, web pages, web page templates, data structures, database tables, repositories storing dynamic information, or other appropriate information including any parameters, variables, algorithms, instructions, rules, constraints, or references. Additionally, the memory can include other appropriate data, such as logs, policies, security or access data, or reporting files. The processor and the memory can be supplemented by, or incorporated in, special purpose logic circuitry.

To provide for interaction with a user, implementations of the subject matter described in this specification can be implemented on a computer having a display device, for example, a CRT (cathode ray tube), LCD (liquid crystal display), LED (Light Emitting Diode), or plasma monitor, for displaying information to the user and a keyboard and a pointing device, for example, a mouse, trackball, or trackpad by which the user can provide input to the computer. Input can also be provided to the computer using a touchscreen, such as a tablet computer surface with pressure sensitivity, a multi-touch screen using capacitive or electric sensing, or another type of touchscreen. Other types of devices can be used to interact with the user. For example, feedback provided to the user can be any form of sensory feedback. Input from the user can be received in any form, including acoustic, speech, or tactile input. In addition, a computer can interact with the user by sending documents to and receiving documents from a client computing device that is used by the user.

The term "graphical user interface," or "GUI," can be used in the singular or the plural to describe one or more graphical user interfaces and each of the displays of a particular graphical user interface. Therefore, a GUI can represent any graphical user interface, including but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a Web browser through which a user can interact with an implementation of the subject matter described in this specification, or any combination of one or more such back-end, middleware, or front-end components. The components of the system can be interconnected by any form or medium of wireline or wireless digital data communication (or a combination of data communication), for example, a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n or 802.20 (or a combination of 802.11x and 802.20 or other protocols consistent with the present disclosure), all or a portion of the Internet, another communication network, or a combination of communication networks. The communication network can communicate with, for example, Internet Protocol (IP) packets, Frame Relay frames, Asynchronous Transfer Mode (ATM) cells, voice, video, data, or other information between networks addresses.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of what can be claimed, but rather as descriptions of features that can be specific to particular implementations. Certain features that are described in this specification in the context of separate implementations can also be implemented, in combination, in a single implementation. Conversely, various features that are described in the context of a single implementation can also be implemented in multiple implementations, separately, or in any sub-combination. Moreover, although previously described features can be described as acting in certain combinations and even initially claimed as such, one or more features from a claimed combination can, in some cases, be excised from the combination, and the claimed combination can be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations can be considered optional), to achieve desirable results. In certain circumstances, multitasking or parallel processing (or a combination of multitasking and parallel processing) can be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

What is claimed is:

1. A computer-implemented method, comprising:
    accessing data from a gas oil separation plant (GOSP) facility, wherein the data includes a first stream of real-time measurements taken from inside the GOSP facility and a second stream of real-time measurements of water cut of the GOSP facility;
    selecting, based on feature engineering, a subset of features corresponding to the first stream of real-time measurements taken from inside the GOSP facility, wherein the subset of features are more strongly correlated with the water cut of the GOSP facility than unselected features;
    based on the subset of features, training a predictive model using the second stream of real-time_measurements of water cut of the GOSP facility;
    applying the predictive model to generate at least one predicted water cut of the GOSP facility as a forecast range for an upcoming period of 15 to 30 minutes based on a third stream of real-time measurements taken from inside the GOSP facility; and
    dynamically presenting the forecast range for the upcoming period of 15 to 30 minutes so that an alert is provided when the forecast range is outside a specified crude quality, which causes treated crude oil exiting the GOSP facility to be maintained at the specified crude quality.

2. The computer-implemented method of claim 1, wherein the third stream of real-time measurements taken from inside the GOSP facility is not included the subset of the real-time measurements taken from inside the GOSP facility, and wherein the at least one predicted water cut of the GOSP facility is not included in the subset of the real-time_measurements of water cut of the GOSP facility.

3. The computer-implemented method of claim 1, wherein the features are selected based on at least one decision tree algorithm that utilizes a Gini importance metric or a mean decrease impurity (MDI) metric.

4. The computer-implemented method of claim 3, wherein the decision tree algorithm assigns a score to each of the features based on how useful each feature is at predicting the water cut of the GOSP facility.

5. The computer-implemented method of claim 4, wherein the decision tree algorithm utilizes at least one permutation of importance against the predictive model being trained.

6. The computer-implemented method of claim 5, wherein the at least one permutation of importance performs shuffling of the features according to respective scores of the features, and wherein the method further comprises:
  evaluating an importance of each feature; and
  ranking the features based on the evaluated importance.

7. The computer-implemented method of claim 5, further comprising:
  identifying features that are strongly correlated such that duplicate features can be trimmed, wherein the features are strongly correlated when a correlation of the features exceed a threshold.

8. A computer system comprising one or more processors, wherein the one or more processors are configured to perform operations of:
  accessing data from a gas oil separation plant (GOSP) facility, wherein the data includes a first stream of real-time measurements taken from inside the GOSP facility and a second stream of real-time measurements of water cut of the GOSP facility;
  selecting, based on feature engineering, a subset of features corresponding to the first stream of real-time measurements taken from inside the GOSP facility, wherein the subset of features are more strongly correlated with the water cut of the GOSP facility than unselected features;
  based on the subset of features, training a predictive model using the second stream of real-time measurements of water cut of the GOSP facility;
  applying the predictive model to generate at least one predicted water cut of the GOSP facility as a forecast range for an upcoming period of 15 to 30 minutes based on a third stream of real-time measurements taken from inside the GOSP facility; and
  dynamically presenting the forecast range for the upcoming period of 15 to 30 minutes so that an alert is provided when the forecast range is outside a specified crude quality, which causes treated crude oil exiting the GOSP facility to be maintained at the specified crude quality.

9. The computer system of claim 8, wherein the third stream of real-time measurements taken from inside the GOSP facility is not included the subset of the real-time measurements taken from inside the GOSP facility, and wherein the at least one predicted water cut of the GOSP facility is not included in the subset of the real-time measurements of water cut of the GOSP facility.

10. The computer system of claim 8, wherein the features are selected based on at least one decision tree algorithm that utilizes a Gini importance metric or a mean decrease impurity (MDI) metric.

11. The computer system of claim 10, wherein the decision tree algorithm assigns a score to each of the features based on how useful each feature is at predicting the water cut of the GOSP facility.

12. The computer system of claim 11, wherein the decision tree algorithm utilizes at least one permutation of importance against the predictive model being trained.

13. The computer system of claim 12, wherein the at least one permutation of importance performs shuffling of the features according to respective scores of the features, and wherein the operations further comprise:
  evaluating an importance of each feature; and
  ranking the features based on the evaluated importance.

14. The computer system of claim 12, wherein the operations further comprise:
  identifying features that are strongly correlated such that duplicate features can be trimmed, wherein the features are strongly correlated when a correlation of the features exceed a threshold.

* * * * *

UNITED STATES PATENT AND TRADEMARK OFFICE
CERTIFICATE OF CORRECTION

PATENT NO. : 12,175,380 B2  
APPLICATION NO. : 17/122736  
DATED : December 24, 2024  
INVENTOR(S) : Abdullah Mohammed Alabdullatif et al.

Page 1 of 1

It is certified that error appears in the above-identified patent and that said Letters Patent is hereby corrected as shown below:

In the Claims

In Column 14, Line 34-35, Claim 1, please replace "real-time_measurements" with -- real-time measurements --

In Column 14, Line 53, Claim 2, please replace "real-time_measurements" with -- real-time measurements --

Signed and Sealed this  
Fourth Day of March, 2025

Coke Morgan Stewart  
*Acting Director of the United States Patent and Trademark Office*